(12) United States Patent
Stanley et al.

(10) Patent No.: US 11,317,901 B2
(45) Date of Patent: *May 3, 2022

(54) VASCULAR CLOSURE WITH MULTIPLE CONNECTIONS

(71) Applicant: Cook Medical Technologies LLC, Bloomington, IN (US)

(72) Inventors: Cleon Stanley, Bloomington, IN (US); Ram H. Paul, Jr., Bloomington, IN (US); Dennis Griffin, Englewood, CO (US)

(73) Assignee: Cook Medical Technologies LLC, Bloomington, IN (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/126,262

(22) Filed: Sep. 10, 2018

(65) Prior Publication Data

US 2019/0000432 A1    Jan. 3, 2019

Related U.S. Application Data

(63) Continuation of application No. 14/056,429, filed on Oct. 17, 2013, now Pat. No. 10,070,850.

(Continued)

(51) Int. Cl.
*A61B 17/00* (2006.01)

(52) U.S. Cl.
CPC ............ *A61B 17/0057* (2013.01); *A61B 2017/00615* (2013.01); *A61B 2017/00619* (2013.01); *A61B 2017/00623* (2013.01)

(58) Field of Classification Search
CPC ............ A61B 17/0057; A61B 17/0401; A61B 2017/0061; A61B 2017/00615;
(Continued)

(56) References Cited

U.S. PATENT DOCUMENTS 4,744,364 A * 5/1988 Kensey .............. A61B 17/0057
604/15
5,269,809 A   12/1993 Hayhurst et al.
(Continued)

FOREIGN PATENT DOCUMENTS

EP    0 534 696 A1    3/1993
EP    1 169 968 A1    1/2002
(Continued)

OTHER PUBLICATIONS

International Search Report and Written Opinion issued in PCT/US2012/066173, dated Mar. 8, 2013.
(Continued)

*Primary Examiner* — Tan-Uyen T Ho
*Assistant Examiner* — Charles M Wei
(74) *Attorney, Agent, or Firm* — Woodard, Emhardt, Henry, Reeves and Wagner LLP (57) ABSTRACT

Among other things, methods and apparatus for inserting devices for closing a tissue opening are disclosed. An anchoring or sealing member has one or more stems and/or filaments that are offset from the center of the member, so that lateral adjustments or movements of the anchoring or sealing member do not uncover the opening, cause the anchoring or sealing member to stick through or pull through the opening. Embodiments including a valve adapted to accommodate a guide wire for addressing emergencies are also disclosed.

18 Claims, 6 Drawing Sheets

Related U.S. Application Data (60) Provisional application No. 61/716,155, filed on Oct. 19, 2012.

(58) Field of Classification Search
CPC .. A61B 2017/00606; A61B 2017/0404; A61B 2017/0419; A61B 2017/00628; A61B 2017/00659; Y10T 24/3685; A61F 2/24–2496
See application file for complete search history.

(56) References Cited

U.S. PATENT DOCUMENTS

| | | | |
|---|---|---|---|
| 5,312,435 A | 5/1994 | Nash et al. | |
| 5,342,393 A | 8/1994 | Stack | |
| 5,350,399 A | 9/1994 | Erlebacher et al. | |
| 5,411,520 A | 5/1995 | Nash et al. | |
| 5,531,759 A | 7/1996 | Kensey et al. | |
| 5,545,178 A | 8/1996 | Kensey et al. | |
| 5,620,461 A | 4/1997 | Muijs Van De Moer | |
| 5,643,320 A * | 7/1997 | Lower | A61B 17/1615 606/232 |
| 5,662,681 A | 9/1997 | Nash et al. | |
| 5,700,277 A | 12/1997 | Nash et al. | |
| 5,800,436 A * | 9/1998 | Lerch | A61B 17/688 606/324 |
| 5,916,236 A | 6/1999 | Muijs Van de Moer et al. | |
| 6,071,301 A | 6/2000 | Cragg et al. | |
| 6,190,400 B1 | 2/2001 | Van De Moer et al. | |
| 6,280,474 B1 * | 8/2001 | Cassidy | A61B 17/0401 623/16.11 |
| 6,426,911 B1 | 7/2002 | Akerfeldt | |
| 6,491,714 B1 | 12/2002 | Bennett | |
| 6,508,828 B1 * | 1/2003 | Akerfeldt | A61B 17/0057 606/215 |
| 6,596,013 B2 | 7/2003 | Yang et al. | |
| 6,712,837 B2 * | 3/2004 | Akerfeldt et al. | A61B 17/0057 606/213 |
| 6,755,868 B2 | 6/2004 | Rousseau | |
| 6,764,500 B1 | 7/2004 | Muijs Van De Moer et al. | |
| 6,780,164 B2 * | 8/2004 | Bergheim | A61F 9/0017 604/8 |
| 6,860,896 B2 | 3/2005 | Akerfeldt et al. | |
| 6,916,333 B2 * | 7/2005 | Schmieding | A61B 17/0401 606/232 |
| 6,921,401 B2 | 7/2005 | Lerch et al. | |
| 6,939,363 B2 | 9/2005 | Akerfeldt | |
| 7,048,710 B1 | 5/2006 | Cragg et al. | |
| 7,169,168 B2 | 1/2007 | Muijs Van De Moer et al. | |
| 7,338,514 B2 | 3/2008 | Wahr et al. | |
| 7,597,706 B2 | 10/2009 | Forsberg et al. | |
| 7,621,937 B2 | 11/2009 | Pipenhagen et al. | |
| 7,658,748 B2 | 2/2010 | Marino et al. | |
| 7,717,929 B2 | 5/2010 | Fallman | |
| 7,875,052 B2 | 1/2011 | Kawaura et al. | |
| 7,931,671 B2 * | 4/2011 | Tenerz | A61B 17/0057 606/151 |
| 7,993,367 B2 | 8/2011 | Bagaolsan et al. | |
| 8,106,352 B2 | 1/2012 | Egnelov | |
| 8,257,389 B2 | 9/2012 | Chanduszko et al. | |
| 8,480,709 B2 | 7/2013 | Chanduszko et al. | |
| 8,500,809 B2 * | 8/2013 | Saliman | A61B 17/0401 623/13.11 |
| 8,652,166 B2 | 2/2014 | Akerfeldt | |
| 8,900,295 B2 * | 12/2014 | Migliazza | A61B 17/0401 623/2.19 |
| 8,920,462 B2 * | 12/2014 | McGuckin, Jr. | A61B 17/0057 606/213 |
| 8,932,325 B2 * | 1/2015 | Stanley | A61B 17/0057 606/213 |
| 10,070,850 B2 * | 9/2018 | Stanley | A61B 17/0057 |
| 2003/0181988 A1 | 9/2003 | Rousseau | |
| 2003/0209835 A1 * | 11/2003 | Chun | A61F 2/2415 264/339 |
| 2004/0093025 A1 * | 5/2004 | Egnelov | A61B 17/0487 606/214 |
| 2004/0230222 A1 * | 11/2004 | van der Burg | A61B 17/12186 606/213 |
| 2005/0085855 A1 | 4/2005 | Forsberg | |
| 2005/0096696 A1 * | 5/2005 | Forsberg | A61B 17/0057 606/213 |
| 2005/0169974 A1 | 8/2005 | Tenerz | |
| 2005/0283187 A1 * | 12/2005 | Longson | A61B 17/0057 606/213 |
| 2005/0283193 A1 * | 12/2005 | Tullberg | A61B 17/00491 606/232 |
| 2006/0142797 A1 | 6/2006 | Egnelov | |
| 2006/0206146 A1 | 9/2006 | Tenerz | |
| 2007/0123936 A1 * | 5/2007 | Goldin | A61B 17/0057 606/232 |
| 2007/0198059 A1 | 8/2007 | Patel et al. | |
| 2008/0033487 A1 * | 2/2008 | Schwartz | A61B 17/0401 606/232 |
| 2008/0071310 A1 | 3/2008 | Hoffman et al. | |
| 2008/0114395 A1 | 5/2008 | Mathisen et al. | |
| 2008/0287986 A1 | 11/2008 | Thor et al. | |
| 2008/0312684 A1 | 12/2008 | Drasler et al. | |
| 2009/0018574 A1 | 1/2009 | Martin | |
| 2009/0054926 A1 | 2/2009 | Pipenhagen et al. | |
| 2009/0088793 A1 | 4/2009 | Bagaolsan et al. | |
| 2009/0112257 A1 | 4/2009 | Preinitz | |
| 2009/0143817 A1 | 6/2009 | Akerfeldt | |
| 2009/0216267 A1 | 8/2009 | Willard et al. | |
| 2009/0234377 A1 | 9/2009 | Mahlin | |
| 2010/0042144 A1 | 2/2010 | Bennett | |
| 2010/0087854 A1 | 4/2010 | Stopek et al. | |
| 2010/0002173 A1 | 8/2010 | Hansen et al. | |
| 2010/0217309 A1 * | 8/2010 | Hansen | A61B 17/0057 606/213 |
| 2011/0066181 A1 | 3/2011 | Jenson et al. | |
| 2011/0082427 A1 * | 4/2011 | Golzarian | A61P 9/00 604/187 |
| 2011/0213414 A1 * | 9/2011 | McGuckin, Jr. | A61B 17/0057 606/213 |
| 2011/0288581 A1 * | 11/2011 | Paul, Jr. | A61B 17/0057 606/213 |
| 2011/0319988 A1 * | 12/2011 | Schankereli | A61F 2/2418 623/2.11 |
| 2012/0116447 A1 | 5/2012 | Stanley et al. | |
| 2013/0079873 A1 * | 3/2013 | Migliazza | A61B 17/0401 623/2.17 |
| 2013/0184811 A1 * | 7/2013 | Rowe | A61F 2/2418 623/2.11 |
| 2014/0018906 A1 * | 1/2014 | Rafiee | A61F 2/24 623/1.26 |
| 2014/0249621 A1 * | 9/2014 | Eidenschink | A61F 2/2418 623/2.11 |
| 2016/0166382 A1 * | 6/2016 | Nguyen | A61F 2/2454 623/2.17 |

FOREIGN PATENT DOCUMENTS

| | | |
|---|---|---|
| EP | 1 266 626 A1 | 12/2002 |
| EP | 1 413 255 A1 | 4/2004 |
| EP | 1 440 661 | 7/2004 |
| EP | 2 064 999 A2 | 6/2009 |
| WO | WO 1999/33402 | 7/1999 |
| WO | WO 2000/078226 | 12/2000 |
| WO | WO 2005/063133 A1 | 7/2005 |
| WO | WO 2006/075228 | 7/2006 |
| WO | WO 2007/059243 A1 | 5/2007 |
| WO | WO 2011/146729 A2 | 11/2011 |

OTHER PUBLICATIONS

International Search Report and Written Opinion issued in PCT/US2011/037173, dated Nov. 17, 2011.

* cited by examiner

VASCULAR CLOSURE WITH MULTIPLE CONNECTIONS

This application is a continuation of Ser. No. 14/056,429, filed Oct. 17, 2013, which claims the benefit of U.S. Provisional Application Ser. No. 61/716,155 (filed on Oct. 19, 2012), which is incorporated herein by reference in its entirety.

The present disclosure concerns closures for openings in bodily tissue. In particular, the disclosure concerns devices for closing relatively large holes in vessels, organs or other locations.

BACKGROUND

In medical procedures involving internal access to blood vessels, it is necessary once the procedure is concluded to prevent substantial bleeding through the opening created and/or maintained by a device (e.g. sheath or introducer) to access the blood vessel interior. External pressure applied via the skin to the vessel has been a primary way to close or minimize the hole so that natural clotting and repair can occur. However, applying such pressure following removal of the access device can result in significant blood loss, is difficult for a physician, nurse or other professional to apply, and can result in minimizing or stopping flow in the vessel, which over time can have negative consequences.

Closures for holes in vascular walls have been proposed that include plugs, seals or other blocking pieces placed in or over the hole. A number of structures and techniques have been proposed for placing and holding such closures, so that minimal amounts of blood escape the vessel. It has been found, however, that such closures can be less efficacious in sealing vascular or other tissue holes that are relatively large. While such closures may work well in closing holes made by small introducers, as for example those used to introduce small catheters for infusion of contrast agents or medicaments, they may not be able to be easily or efficiently placed to close larger openings, as for example those made by introducers for intra-aortic balloon (IAB) pump or abdominal aortic aneurysm (AAA) repair. Existing closures may be poorly centered over a hole, allowing a portion of the hole to be uncovered, or a portion of the closure may bend due to blood flow, creating a gap between the closure and the vessel tissue. In such cases, leakage of blood and resultant complications can occur.

Likewise, other types of relatively large tissue openings (e.g. patent foramen ovale (PFO), fistulae, or the like) present difficulties for closure by existing devices. Accordingly, there is a need for improvement in this area.

SUMMARY

Among other things, there are disclosed medical treatment devices for a tissue opening in a patient. Particular embodiments of such devices include an anchoring member adapted for engagement with tissue bordering the tissue opening, and at least first and second filaments connected to the anchoring member and adapted to extend from the anchoring member to a position outside of the patient, so that pulling one or more of the filaments tends to engage or press the anchoring member against the tissue. The anchoring member has a center point inside at least one edge, with the connection of the first filament and the anchoring member being offset laterally in a first direction from the center point, and the connection of the second filament and the anchoring member offset laterally in a second direction from the center point. The first and second directions may be substantially opposed to each other, and the distance between the first and second filaments may be less than or equal to a dimension of the tissue opening.

As particular examples, the anchoring member includes at least first and second stems monolithic with the remainder of the anchoring member, with the first filament is attached to the first stem and the second filament is attached to the second stem. The anchoring member may have a major axis through the center point and extending between first and second ends of the anchoring member, and the first and second stems are on that major axis. The first and second stems can be equidistant from the center point. Embodiments in which the anchoring member includes at least three, four or more stems, each having a respective filament, each displaced from the center point by approximately the same distance, and each separated from adjacent stems by approximately the same distance and/or angle are also contemplated. Certain embodiments of the anchoring member include a hemostatic valve adapted to permit passage of a guide wire therethrough, the valve substantially preventing blood flow through the anchoring member. The valve may be placed substantially at the center point of the anchoring member or its wall, and be offset from each of said first and second filaments. A guide wire may be provided that extends through the valve.

In particular embodiments, including embodiments in which an anchoring or sealing member has a single stem or filament, a system or apparatus may include a pusher with a lumen. The pusher is configured to move over the stem with at least a portion of the stem within the lumen, and has a forward portion that is inwardly tapered. In embodiments in which a filament is connected with the stem, a pusher can be provided with a lumen and configured to move over the stem and filament with at least a portion of the stem and at least portion of the filament within the lumen. An indicator is fixed with respect to at least one of the stem and filament and at least partially within the pusher, the indicator having at least a portion contrasting with the pusher. The indicator is positioned to exit from the pusher as the pusher is moved along at least one of the stem and the filament so that the contrasting portion exits from the pusher at a point at which the pusher has moved a desired distance, such as a distance necessary to lock the anchoring or sealing member in place against tissue.

Other examples of medical treatment devices for a tissue opening in a patient include an anchoring member adapted for engagement with tissue bordering the tissue opening, the anchoring member including a wall, the wall having a valve portion allowing penetration through the wall and providing hemostatic control. A guide wire is inserted through the valve so that a portion of the guide wire is on either side of the wall, wherein when the anchoring member is engaged with tissue bordering the tissue opening, a portion of the guide wire extends through the opening. Such an anchoring member can include at least one stem monolithic with the wall and offset from the valve, e.g. at least first and second stems joined to the wall and offset from the valve, wherein the first and second stems and the valve are along a line. In such embodiments, a first distance between the first stem and the valve and a second distance between the second stem and the valve may be substantially the same, and/or the distance between the first and second stems may be equal to or less than a dimension of the tissue opening. A first filament can be connected to the first stem and a second filament connected to the second stem, or at least one filament connected to the anchoring member and offset from the valve.

Methods for treating an opening in tissue are also disclosed, and in particular embodiments include inserting through the opening a medical treatment device having an anchoring member and at least first and second filaments connected to the anchoring member and adapted to extend from the anchoring member to a position outside of the patient. The anchoring member has a center point, with the connection of the first filament and the anchoring member offset laterally in a first direction from the center point, and the connection of the second filament and the anchoring member offset laterally in a second direction from the center point, with the first and second directions substantially opposed to each other, so that the first and second filament extend to a location outside the patient. The user provides tension on the first and second filaments so that the anchoring member is firmly engaged with tissue adjacent the opening, one or more of the anchoring member and the filaments preventing movement of the anchoring member with respect to the opening to the degree that an end of the anchoring member is within the hole. The anchoring member is locked in place with respect to the tissue. Methods can also include, with the anchoring member having first and second stems and the first filament is attached to the first stem and the second filament is attached to the second stem, an inserting step that includes placing the anchoring member so that the first and second stems both extend through the hole so that the stems limit movement of the anchoring member with respect to the hole. With the anchoring member having a hemostatic valve and a guide wire extending through the valve, methods can include monitoring the treatment of the tissue opening, and where an emergency is detected, applying a medical device over the guide wire to one or both of the tissue and the hole.

Devices and methods as described herein provide solutions to problems existing with some types of vascular closure devices, including risks of improper placement of the device so that an opening is not closed or covered sufficiently, and of damage or eversion of a closure when tension is applied. The multiple connections of the disclosure distribute pulling force through the connections, making it less likely for any particular connection to fail, or for too much force at one point to cause an eversion or pull-through of a closure device. Further, in cases where failure of the treatment occurs, emergency measures must be taken, and structure to facilitate such measures is also disclosed.

DESCRIPTION OF THE ILLUSTRATED EMBODIMENTS

To promote an understanding of the principles of the disclosure, reference will now be made to certain embodiments and specific language will be used to describe the same. It will nevertheless be understood that no limitation of the scope of the claims is thereby intended, such alterations and further modifications of the disclosed methods and/or devices, and such further applications of the principles of the disclosure as described herein, being contemplated as would normally occur to one skilled in the art to which the disclosure relates.

Figure 1:
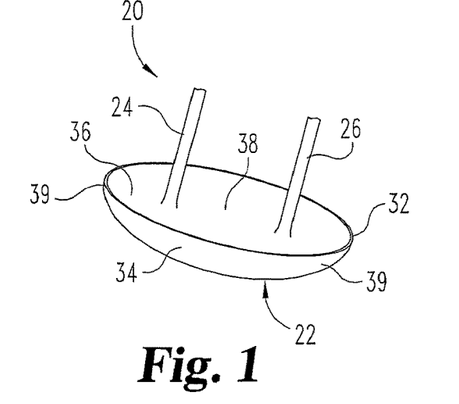
FIG. 1 is a perspective view of an embodiment of a device or part of a system for closing bodily openings.

Referring now generally to FIG. 1, there is shown an embodiment of a closure device 20 for use itself or with a system for closing holes in tissue, such as those formed in the walls of blood vessels during catheterizations or other treatments, or septal defects (e.g. patent foramen ovale, or PFO). Embodiments of device 20 can be used for closing holes of any size, whether relatively small or relatively large. However, device 20 is believed to be effective in closing large or elongated holes, where existing devices are not or present difficulties or uncertainties in closing such holes.

Device 20 includes an internal anchoring or sealing member 22 that is placed on one side of a hole to be closed (e.g. within a blood vessel) and at least two elongated members (e.g. members 24, 26 in FIGS. 1-3) extending proximally from anchoring member 22. As will be discussed further below, elongated members 24, 26 may be stems that are part of or are fixed to anchoring member 22, or may be threads or other types of filaments attached to anchoring member 22.

Anchoring or sealing member 22 in the illustrated embodiment is in the illustrated embodiment is a curved toggle or dome having a wall 30. Wall 30 can have a constant or varying thickness, for example in certain embodiments having a maximum thickness in the range of about 0.0050 inches to about 0.050 inches, and in a particular embodiment about 0.015 inches. In the illustrated embodiment, the maximum thickness of member 22 is at and/or between the connection(s) with elongated members 24 and 26 are, and the thickness decreases uniformly out to a rim 32. Anchoring or sealing member 22 is part-spheroidal in an unstressed state (e.g. FIGS. 1-3), having a substantially oval-shaped (e.g. elliptical) rim 32. Rim 32 is substantially in one plane in this embodiment, having little or no breadth. Member 22 has an exterior convex surface 34 and an interior concave surface 36 which is open and unobstructed. In particular embodiments, surfaces 34 and 36 may have substantially the same radii, so that the overall thickness of wall 30 is substantially constant, or may have differing radii, so that they intersect or approach each other at (and wall 32 thins toward) rim 32. A center point 38 may have a tangent plane that is parallel to the plane of rim 32. An elongated toggle or dome member 22 has respective ends or end portions 39 along a major axis MA, so that the distance between ends 39 is the largest dimension of member 22.

Figure 1A:
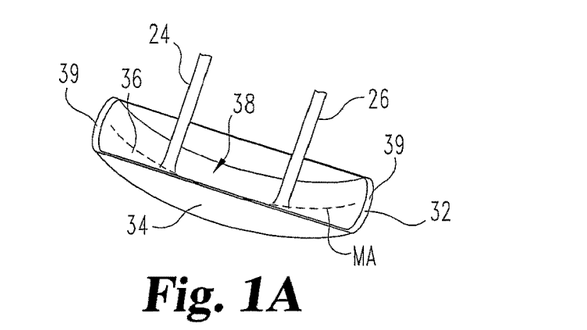
FIG. 1A is a perspective view of an embodiment of a device or part of a system for closing bodily openings.
Figure 2:
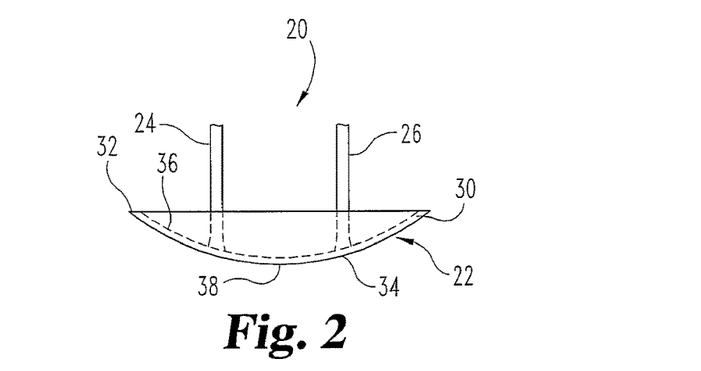
FIG. 2 is a side view of the embodiment of FIG. 1.
Figure 3:
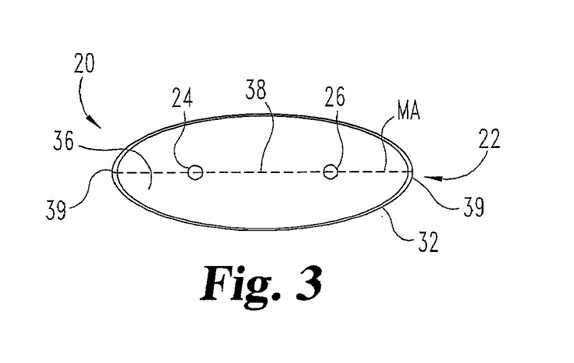
FIG. 3 is a top view of the embodiment of FIG. 1.

FIG. 1A shows an example of an anchoring member 22 that is essentially the same as member 22 in FIGS. 1-3, with the exception that the generally elliptical form of the embodiment in FIGS. 1-3 is truncated substantially along the major axis MA, leaving an anchoring member in the form of a toggle. Rim 32 around end portions 39 may thus form part of an ellipse. Exterior convex surface 34, interior concave surface 36 and center point 38 as described above may be seen in this example.

In embodiments in which anchoring member 22 is flexible, such flexibility permits an elastic or inelastic deformation or change in shape. Under stress, as discussed further below, internal anchoring or sealing member 22 can be folded for placement in a delivery device, and during or after placement can open or flatten from the folded condition to move close or closer to tissue. Member 22 can be constructed so as to completely flatten (e.g. surface 36 substantially conforming to surrounding tissue) under stress as experienced after implantation, or so as to not completely flatten under such stress (e.g. maintaining an at least slightly concave surface 36 or arch) in use, as discussed further below.

The illustrated embodiment of anchoring or sealing member 22 is made of a flexible material that is biocompatible and resorbable in particular embodiments. In certain embodiments a flexible material is used that is elastically foldable, i.e. that can be folded or compressed into a tube or other holder, and will resume the original dome-like shape once moved out of the holder. Specific examples of materials that have been found to be particularly useful are mixtures of polycaprolactone and L-lactide as disclosed in Application Ser. No. 61/716,182, filed on Oct. 19, 2012, which is incorporated by reference herein in its entirety.

Figure 4:
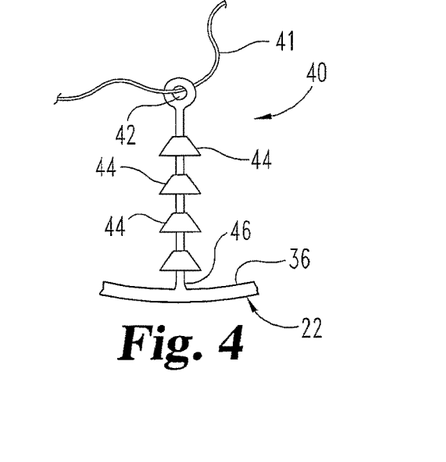
FIG. 4 is a side view of a portion of an embodiment similar to that of FIG. 1 showing an embodiment of an elongated member formed as a stem.

As noted previously, examples of elongated members 24 include filaments and/or stems attached to member 22. For embodiments in which elongated members 24 are or include stems, an exemplary stem 40 is shown in FIG. 4, which is unitary (i.e. monolithic) with or joined to surface 36 or other part of member 22. As discussed further below, additional stems may be provided on member 22 in other embodiments. Each stem 40 in this embodiment is configured to attach to a suture, thread or other filament 41, and in the example of FIG. 4 stems 40 each include an eyelet 42 through which such a filament 41 is threaded. Stems 40 further include protrusions or beads 44 at particular intervals between eyelet 42 and surface 36, and preferably between eyelet 42 and a plane in which rim 32 of member 22 is located. Stems 40 have thickened bases 46 in particular embodiments. In the embodiment of FIG. 4, for example, a base 46 of a stem 40 is conical or outwardly flared from stem 40 toward surface 36. The widened base 46 provides a sturdier or more secure connection between stem 40 and the rest of member 22, which may be needed with greater strains associated with larger vascular or other openings to be closed. A conical or flared base 46 can also provide a non-edged and larger surface against which tissue surrounding the hole can abut. The bases 46 can be lodged against the tissue surrounding the hole, ensuring the positioning of member 22 across the hole while spreading out stress on the tissue.

Elongated members 24, 26 are substantially identical to each other in the illustrated embodiments, e.g. each of elongated members 24, 26 as a stem (e.g. stem 40) to which a suture or other type of filament or fiber is attached. Filament 41 extends proximally from stem 40 (and/or from surface 36 of member 22, e.g. if elongated members 24, 26 are connected directly to surface 36) a distance that is at least sufficient to stretch from an implanted location of member 22 (e.g. within a vessel) to a location outside the patient's body. As indicated above, filament 41 may be directly connected to stem 40, as by threading or looping through eyelet 42 so that filament 41 doubles up on itself, or by fixing filament 41 directly to stem 40 as by welding, gluing, or the like.

The embodiment of FIG. 1 shows an elongated internal anchoring or sealing member 22, substantially in an oval or elliptical shape when viewed from top or bottom (e.g. FIG. 3). Elongated members 24, 26 (e.g. stem 40) are on opposite sides of the center point 38 of sealing member 22. For example, in the embodiment of FIGS. 1-3 in which sealing member 22 is substantially elliptical and has a major axis MA, elongated members 24 are joined to sealing member 22 so that they intersect major axis MA. In a particular case, elongated members 24 are located at or intersecting the foci of the ellipse. In other cases, elongated members 24 may each be located approximately halfway between the center 38 and a respective end 39 of sealing member 22. As indicated, sealing member 22 is intended to be larger in size or outermost extent than an opening in a vessel or other body part to be closed. Particular embodiments of sealing member 22 will have respective elongated members 24, 26 separated by a distance that is less than or approximately equal to the diameter of an introducer used for access to a vessel, and thus less than or approximately equal to the diameter of the opening in the vessel to be closed by member 22.

As noted above, embodiments of anchoring or sealing members 22 having more than two elongated members 24, 26 are contemplated. The embodiments of FIGS. 5, 6, and 9, for example, show a sealing member 22 with four elongated members 24 attached to it, each offset from the center 38 and from the major axis MA. That embodiment shows the placement of elongated members 24 is such that an adjacent pair of elongated members 24 (e.g. toward the top or bottom in FIG. 9) is on a line substantially parallel to axis MA, an adjacent pair of elongated members 24 (e.g. to the right or left in FIG. 9) is on a line substantially perpendicular to axis MA. Opposing or diagonal pairs of elongated members 24 are on lines through center 38 in the illustrated embodiment. Such embodiments space out the application of force through elongated members 24 to sealing member 22, resulting in better attachment of the entirety of sealing member 22 to the inside of the vessel or to other tissue when tension is applied to elongated members 24.

Figure 5:
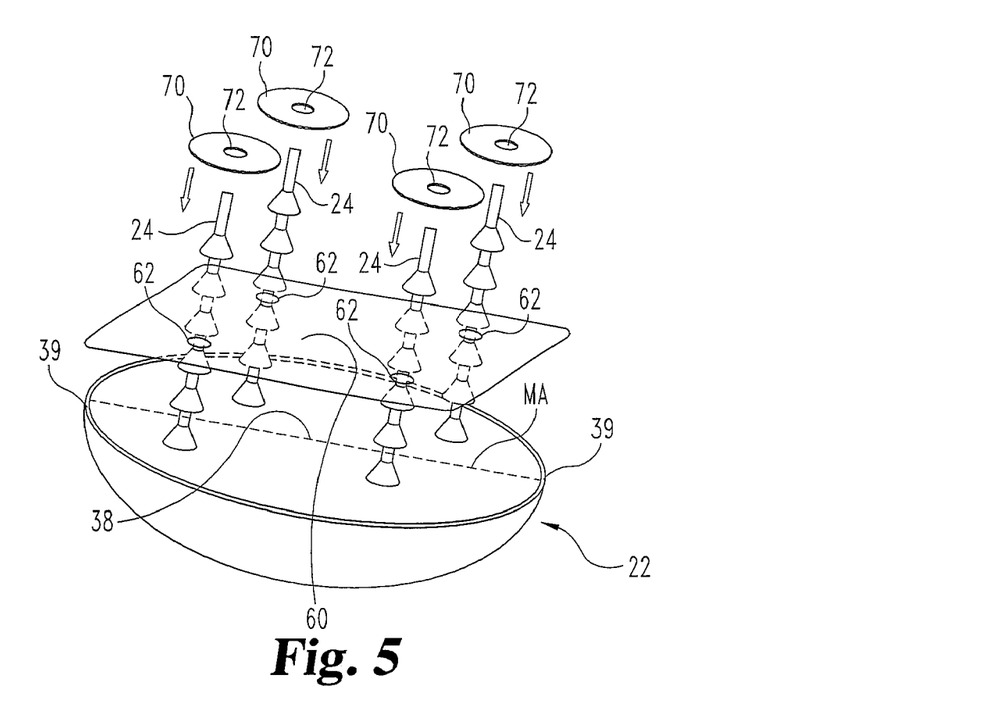
FIG. 5 is a perspective view of an embodiment of a device or part of a system for closing bodily openings.
Figure 6:
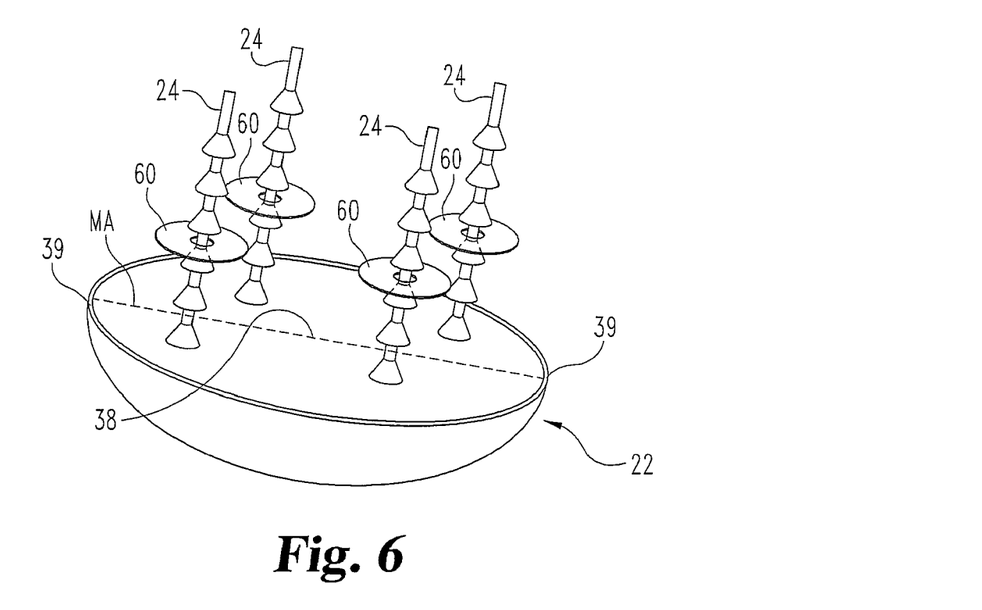
FIG. 6 is a perspective view of an embodiment similar to that of FIG. 5 with a different example of buffer configuration.

One or more portions of buffer material 60 are included in the embodiments shown in FIGS. 5-6. Such buffers 60 are made of biocompatible material, and preferably resorbable material. In particular embodiments, buffers 60 are of small intestinal submucosa (SIS) material. Referring to FIG. 5, buffer 60 is a single sheet or layer with multiple holes 62 positioned in locations compatible with loading buffer 60 onto elongated members 24 of an anchoring or sealing member 22. One or more locking members 70 with central holes 72 are provided to slide over elongated members 24 to lock buffer 60 into place with respect to anchoring or sealing member 22, and member 22 with respect to the hole in tissue. Referring to FIG. 6, a plurality of buffer pieces 60, in the form of flat discs or plates in the illustrated embodiment, are provided. As seen in that figure, one buffer piece 60 can be provided for each stem 40, with a specific locking member 70 for each elongated member 24. It will be understood that in other embodiments multiple buffer pieces 60 may be provided to one or more elongated members 24, and that no buffer piece 60 may be provided to one or more elongated members 24. In particular embodiments, the width or diameter of buffer pieces 60 may be chosen so that portions of two or more such pieces 60 overlap when they are placed along their respective elongated members 24 (see e.g. FIG. 6). Locking members 70, in particular embodiments, are sized and/or configured so that they do not overlap when placed on respective elongated members 24. For example, where stems 40 are separated by a specific distance, the radius of an exemplary locking member 70 may be half or less of that specific distance. In other embodiments, a single locking member 70 may be provided with multiple holes 72 positioned so that the single locking member 70 can be used with multiple elongated members 24.

Figure 7:
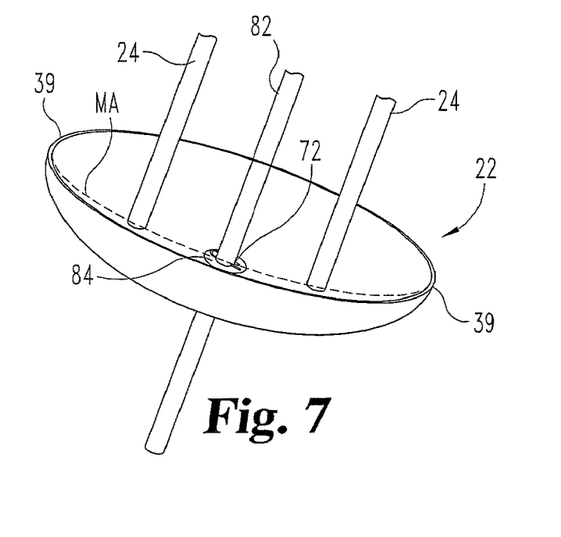
FIG. 7 is a perspective view of an embodiment as in FIG. 1 including additional features.
Figure 7A:
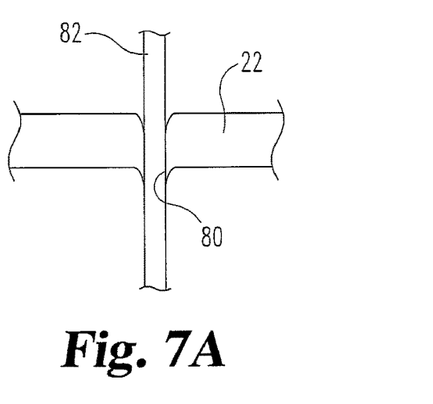
FIG. 7A is a side view of an embodiment of a valve or seal configuration usable in the disclosed embodiments.
Figure 7B:
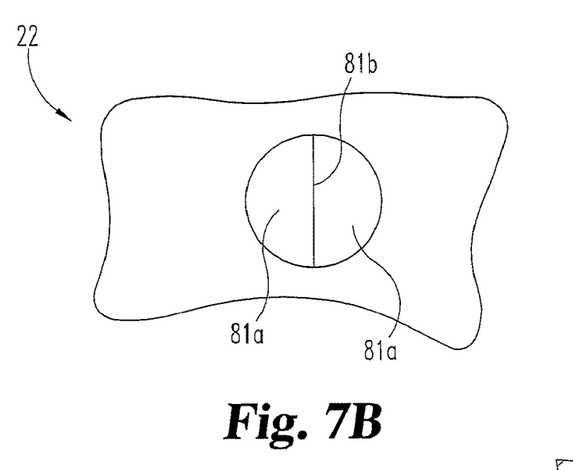
FIG. 7B-D are a top view (FIG. 7B) and part cross-sectional views perpendicular to a slit (FIG. 7C-D) of an embodiment of a valve or seal configuration usable in the disclosed embodiments.
Figure 7C:
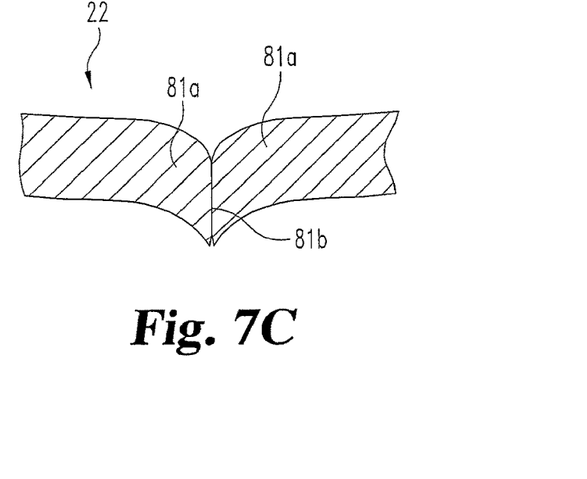
Figure 7D:
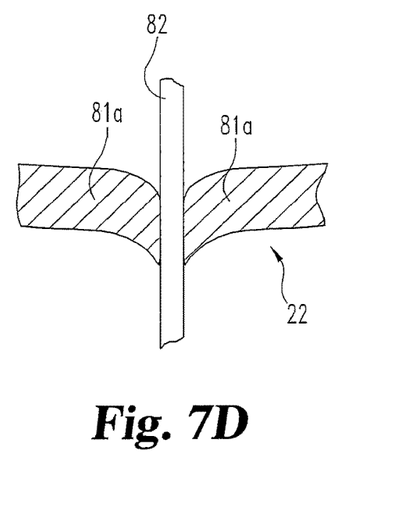
Figure 7E:
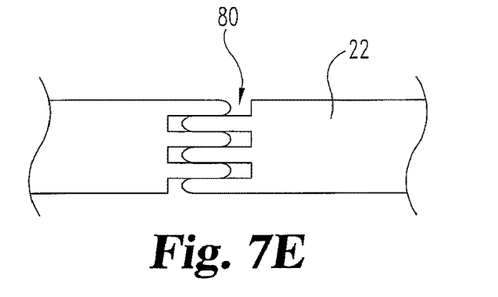
FIG. 7E-F are side views of an embodiment of a valve or seal configuration usable in the disclosed embodiments.
Figure 7F:
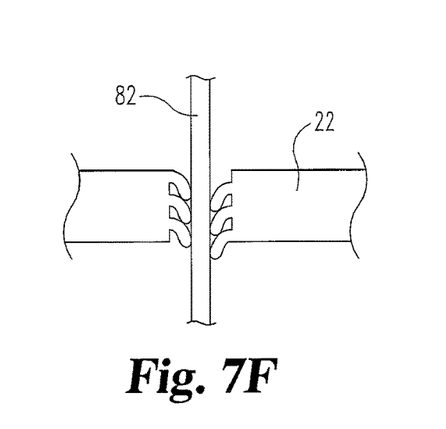
Figure 7G:
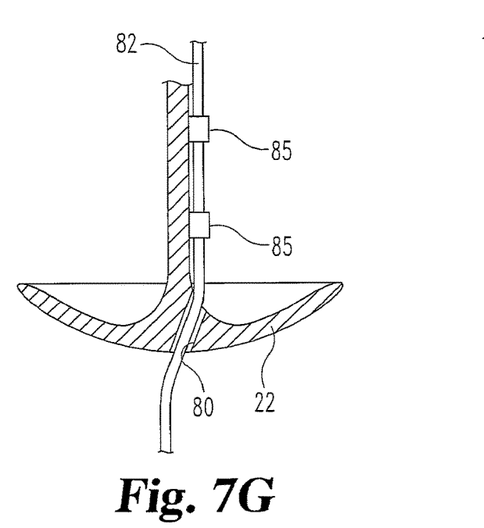
FIGS. 7G-7H are part cross-sectional views of embodiments of valve or seal configurations and connections usable in the disclosed embodiments.
Figure 7H:
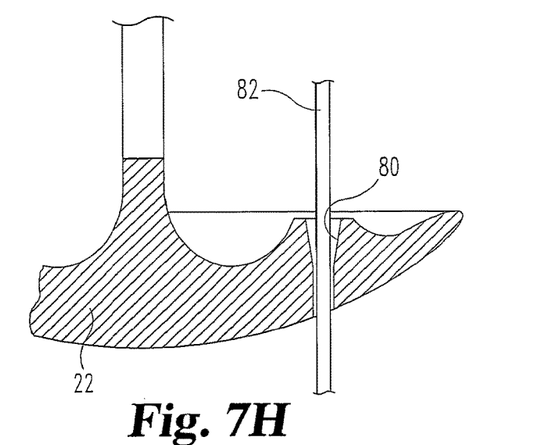
Figure 8:
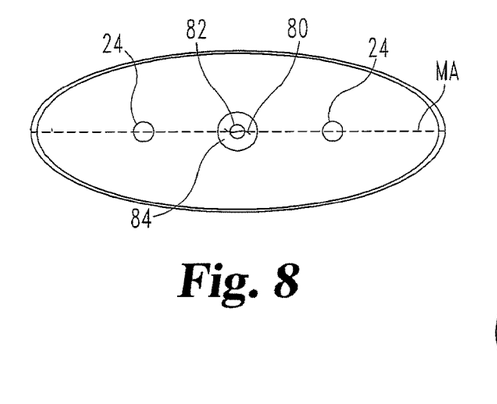
FIG. 8 is a top view of the embodiment of FIG. 7.
Figure 9:
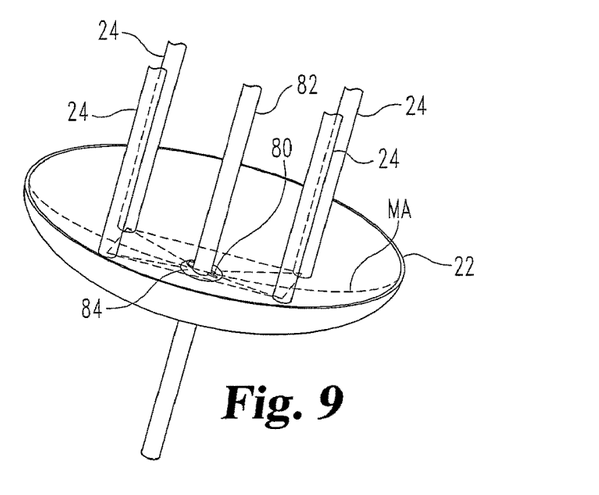
FIG. 9 is a perspective view of an embodiment similar to that of FIG. 5 with features shown in FIG. 7.

Embodiments of anchoring or sealing member 22, shown in examples in FIGS. 7-9, may also include an opening 80 for passage of a guide wire 82. The illustrated embodiment shows opening 80 in the center 38 (unmarked in FIGS. 7-9 to maintain clarity) of member 22. In other respects, this embodiment of member 22 is essentially the same as embodiments described above, with elongated members 24 (e.g. stems 40) offset from the center. Hole 80 in this embodiment is occupied by or includes a valve or seal 84 configured for hemostatic control both when guide wire 82 is inserted through it and when no guide wire is present. Exemplary valves or seals may include an opening through member 22 having at least a portion with a diameter less than the diameter of a guide wire to be extended through it, so that member 22 engages the wire with some force. Such a hole may be cylindrical (e.g. FIG. 7A), a "duck-bill" configuration (e.g. FIG. 7B-D), conical (e.g. FIG. 7H, with the smallest diameter on the concave exterior of member 22), or otherwise configured. A "duck-bill" configuration includes two leaves 81a pressed against each other at a slit 81b, with the leaves generally pointed or oriented toward an outer or exterior surface of member 22. A guide wire 82 through slit 81b is engaged by leaves 81a, and when wire 82 is removed, the leaves press the slit closed to limit or eliminate leakage. A conical opening configuration as indicated in FIG. 7E pinches together as member 22 is pulled against the vascular wall, to limit or eliminate leakage through the opening. Another example of a suitable valve or seal would be an opening with opposed interdigitating (i.e. overlapping) flanges or fingers (e.g. FIG. 7E-F). Wire 82 inserted through the hole bends the flanges or fingers, with the flanges or fingers pressed against the wire to maintain a seal. When wire 82 is withdrawn, the overlapping nature of the flanges or fingers prevents or limits flow through the hole. In other embodiments, a stem 24 and/or 26 may have guides 85 attached to allow passage of wire 82 close to and along the stem (e.g. FIG. 7G). Further, it will be understood that a center opening for passage of wire 82 through member 22 may be adjacent or under a stem (e.g. FIG. 7G), whether the stem is at or offset from the center of member 22, and that an opening for a wire 82 may be offset from the center of member 22. The opening for wire 82 may have a wall thicker than that of member 22 (e.g. FIG. 7H).

It has been noted that, with the sizes of vascular holes for which member 22 is intended, there is the potential for substantial or massive blood loss if the member 22 or another part of device 20 is improperly placed or otherwise does not operate as intended. Guide wire 82 is not used for placement of anchoring or sealing member 22 in some embodiments, but merely accompanies member 22 as it is placed, to provide a safety measure in maintaining vessel access in case of an emergency. That is, should there be a breakage or improper placement of member 22 or another part of device 20 or other emergency, guide wire 82 extends through member 22 and into the vessel, and permits insertion of an emergency sheath, valve, plug or other device to address the situation. While FIGS. 7 and 8 show an embodiment with two elongated members 24, similar to the embodiment in FIGS. 1-3, FIG. 9 shows an embodiment with four elongated members 24, similar to the embodiments shown in FIGS. 5-6. It will be understood that wire and valve usage as noted above can be incorporated into members 22 with a single elongated member 24 placed in the center of member 22.

In addition to a force-spreading characteristic of the multiple elongated members 24, their use in connection with distance between them provides a better opportunity for ensuring proper placement or centering of anchoring or sealing member 22 with respect to a tissue hole. The multiple filament and/or stem embodiments do not permit member 22 to be placed in or to slide to a position in which the hole is not covered, or in which an end 39 of member 22 is in or positioned through the hole. Rather, the presence of spread-apart multiple stems or filaments that extend through the hole means that position or movement of member 22 relative to the hole is limited. The member 22 is less likely to be mispositioned, because of interference between the tissue surrounding the hole and the stems or filaments.

Insertion of embodiments of sealing or anchoring member 22 can be accomplished using devices (e.g. cannulas, catheters, or the like) known for providing access to bodily openings in blood vessels, organs or other tissues. Device 20 is inserted through the opening to be closed, and is retracted so that at least a portion of rim 32 and perhaps at least a portion of inner surface 36 engages tissue. The multiple elongated members 24 help to ensure proper positioning of device 20, i.e. with a portion of member 22 on opposing sides of the hole or surrounding the hole, so that member 22 firmly engages tissue and does not slip back through the hole. That is, elongated members 24 prevent shifting of member 22 into an unacceptable position relative to the hole due to interference with the sides of the hole. Once the member 22 is positioned, buffer 60 may be moved along elongated members 24 by or prior to locking members 70. With locking members 70 engaging elongated members 24 and holding buffer 60 and member 22 over the hole and/or engaging tissue around the hole, the hole is closed. Filaments 41 extending from elongated members 24 (or elongated members 24 themselves if they are filaments) are cut and pulled out of the patient, and the pathway through the skin used to access the bodily opening is closed.

Figure 10:
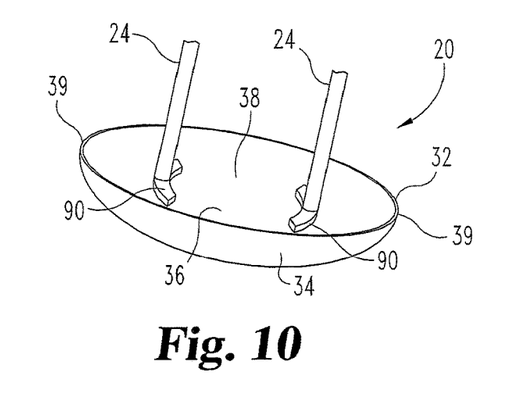
FIG. 10 is a perspective view of an embodiment as in FIG. 1 with additional features.

FIG. 10 depicts an example of an internal anchoring or sealing member 22 similar to that shown in FIGS. 1-3, and common elements described above with respect to FIGS. 1-3 will not be repeated here. In this embodiment, a respective base member 90 is joined to or part of each elongated member 24 and joined to or part of inner surface 36 of member 22. It will be understood that less than all of the elongated members 24 may have such a base member 90 in other embodiments. In the particular example, base members 90 are solid parts that are curved substantially along the curvature of surface 36, e.g. forming a part of an ellipse concentric with an elliptical rim 32 of member 22. Such base members can not only reinforce the connection between elongated members 24 and wall 30 of member 22, but can also help to better index the elongated members 24 within the bodily opening during deployment. The illustrated example of base members 90, which are rounded or part elliptical, can help index with respect to the bodily opening by lying adjacent or engaging a rim of the opening. That is, a side surface of members 90 generally facing rim 32 of member 22 can engage or face the sides of the tissue opening. The sides of members 90 can provide a larger surface to help prevent migration of member 22 or provide some frictional securing of member 22 within the tissue opening.

Figure 11:
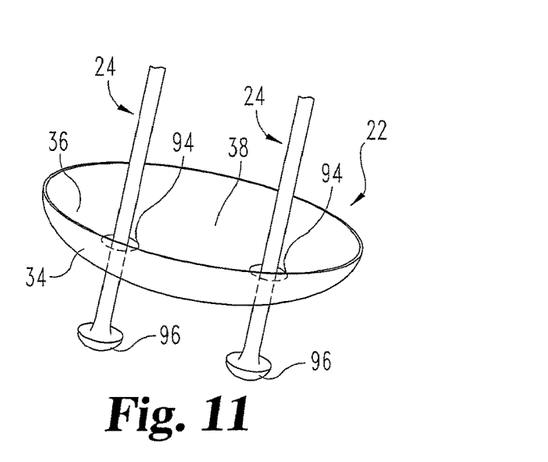
FIG. 11 is a perspective view of an embodiment of a device or part of a system for closing bodily openings.
Figure 12:
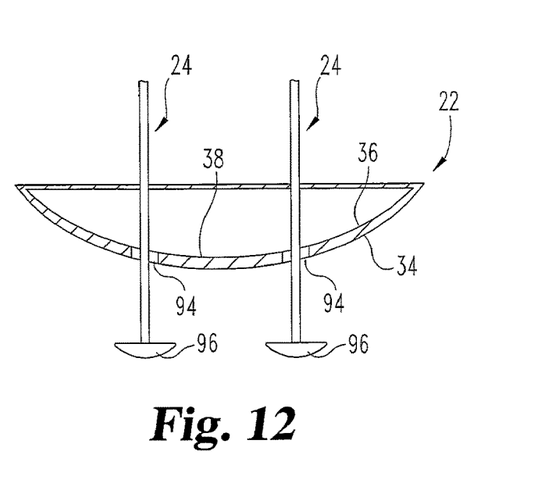
FIG. 12 is a part-sectional view of the embodiment of FIG. 11.

FIGS. 11 and 12 show an example of an embodiment of device 20 in which elongated members 24 are not fixed with respect to anchoring or sealing member 22. In that example, member 22 is similar to that described with respect to FIGS. 1-3, e.g. wall 30 and other parts excepting elongated members 24 and the presence of holes 94. In this embodiment, holes 94 are placed at or near the foci of an elliptical or ellipsoidal member 22. Elongated members 24 in the embodiment of FIGS. 11-12 may be a stem or filament as described above, with a dome-like seal 96 at a distal end. Each seal 96 is sized and configured to cover a respective hole 94, and may be formed as a smaller and/or circular version of member 22 described above. Pulling on one or both of elongated members 24 move the respective seal(s) 96 to and/or over respective holes 94, to prevent leakage through holes 94 and/or to move member 22 against tissue to cover all or part of a bodily opening.

Figure 13A:
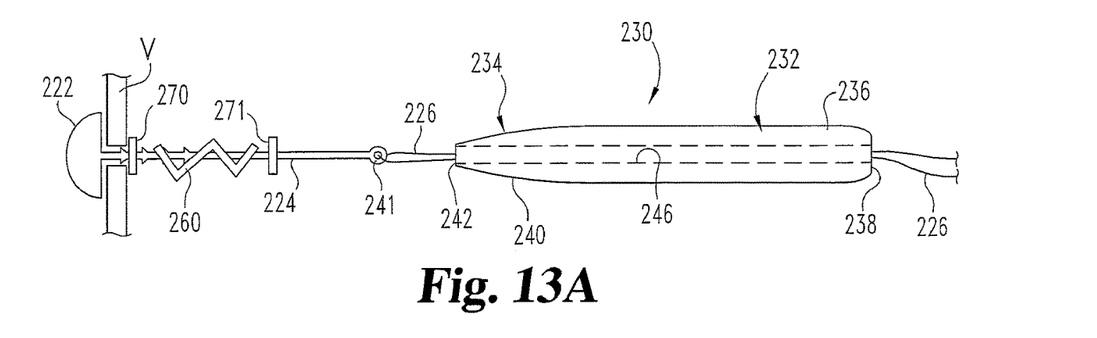
FIG. 13A-B are side views of an embodiment of at least part of a closure system.
Figure 13B:
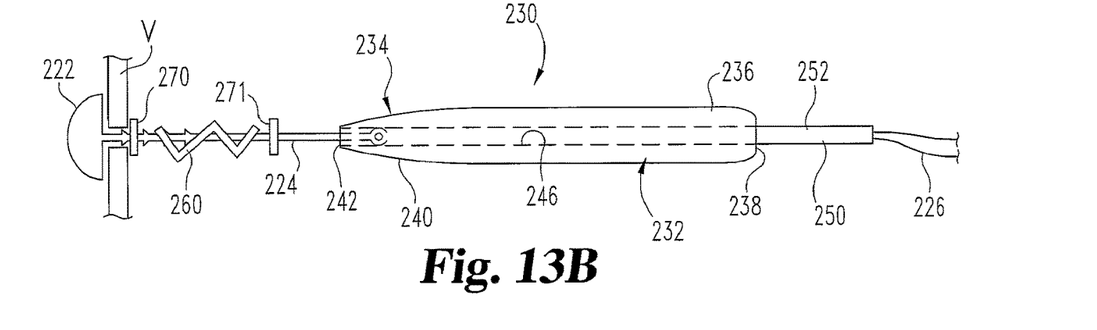
Figure 13C:
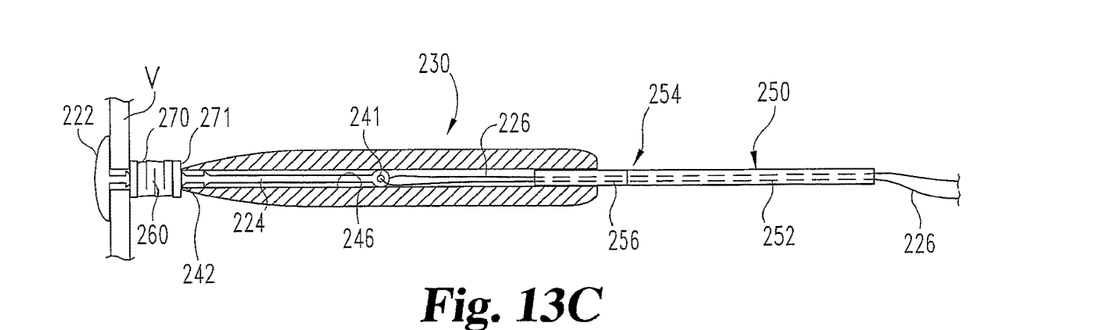
FIG. 13C is a part cross-sectional view of the embodiment of FIG. 13A-B.

FIG. 13A-C show an embodiment of at least part of a closure system having an internal or distal sealing or anchoring member 222, from which a stem 224 with an eyelet 241 and a filament 226 through eyelet 241 extend proximally. Along stem 224 and/or filament 226 are a holding disc 270, a sheet or other mass of buffer material 260 (e.g. small intestine submucosa, or SIS), and a locking disc 271. A pusher 230 is provided to move along filament 226 and/or stem 224 to move at least disc 271 and buffer material 260 along stem 224 and/or filament 226, to lock the system (e.g. with buffer 260 pressed between discs 270 and 271, and a portion of a vessel V or other tissue between disc 270 and member 222). This embodiment may be or include features as disclosed above (e.g. multiple elongated stems, filaments or other members) or as disclosed in application Ser. No. 13/111,338 (filed on May 19, 2011) and Ser. No. 13/303,707 (filed on Nov. 23, 2011), incorporated herein by reference in their entireties.

Embodiments of a pusher device having a substantially cylindrical outer form, with a central lumen to allow the pusher device to slide along and over at least a part of a filament and/or stem connected to a member 22 have been tried. In testing, it was found that such a cylindrical pusher operated well so long as tissue planes intersecting the wound or channel through the skin were generally oriented so that the wound or channel was itself substantially cylindrical. In other cases, such a cylindrical pusher device could catch on or be impeded by the tissue planes.

To resolve that issue, pusher device 230 is substantially torpedo-shaped, having a rearward gripping or base portion 232 and a forward pushing portion 234. Base portion 232 has a substantially cylindrical outer surface 236 in this embodiment, with a rearward or proximal end 238 that is rounded. The illustrated embodiment of forward portion 234 has an outer surface 240 that transitions smoothly with surface 236 of gripping portion 232, and tapers inward toward forward end 242. In particular embodiments, the tapering outer surface 240 describes a portion of a regular circular cone (i.e. a plane tangent to surface 240 intersects surface 240 in a line) or a convex solid (e.g. a plane tangent to surface 240 intersects surface 240 in a point, or a plane including the longitudinal axis of pusher 230 intersects surface 240 in a curve such as a parabola). Pusher 230 has a linear lumen 246 extending between ends 238 and 242. Lumen 246 may have a substantially constant diameter between ends 238 and 242, and in such cases the thickness of the wall of pusher 230 (i.e. the material between lumen 246 and outer surfaces 236, 240) decreases in tapering forward portion 234 as one approaches end 242. In other embodiments, lumen 246 may decrease in diameter in forward portion 234, so that the wall has a smaller or no decrease in width. However, in such cases the diameter of lumen 246 remains large enough to accommodate the filament and/or stem parts over which it is to pass in locking the closure device. End 242 may be rounded in particular embodiments.

Pusher 230 or other parts of the system in particular embodiments can also provide the user an indication as to when locking disc 271 and/or other items are in a desired placement and he or she can thus stop pushing. For example, in the embodiment of FIG. 13A-C an indicator 250 is placed within lumen 246 of pusher 230. Indicator 250 is fixed to one or both of filament 226 and stem 224 connected to anchor or closure member 22, and in the illustrated embodiment is fixed to filament 226. Pusher 230 is movable with respect to filament 226 and stem 224, and is thus also movable with respect to indicator 250. Indicator 250 in the illustrated embodiment is a tube having a proximal portion 252 and a forward or distal portion 254. In other embodiments, indicator 250 may be a sheet, wrap (e.g. a shrink-wrap plastic film), or other attachment.

At least a portion of indicator 250 has a contrasting surface or portion 256 differentiating it from proximal end 238 or more of base portion 232 of pusher 230, as by contrasting coloration, lineation, writing, texture, or other observable features. The illustrated embodiment of indicator 250 includes contrasting portion 256 at or toward distal portion 254, so that use of pusher uncovers a substantial portion of indicator 250 before contrasting portion 256 is exposed from pusher 230. It will be understood that in other embodiments all of indicator 250, or at least a part of proximal portion 252, may be included in contrasting portion 256, so that the contrasting portion 256 is observable as soon as any part of indicator 250 exits from pusher 230. The length and positioning of indicator 250, or the ratio or other relationship of its length with that of pusher 230, are chosen so that when end 242 of pusher 230 is in a position as indicated in FIG. 13C, having pushed disc 271 and buffer 260 against disc 270 and/or tissue, so that the system is locked with respect to member 222 and its filament 226 and/or stem 224, at least a portion of the contrasting part 256 is exposed from the proximal end 238 of pusher 230, observable to the user. Thus, when the user sees contrasting part 256, or a specified amount of part 256, he or she knows that the system is locked as intended. The user is accordingly not limited to relying on resistance felt through the pusher to determine when the locking disc and other items are fully deployed (e.g. snug against the vessel or other tissue against which the anchoring or sealing member 222 was engaged).

To summarize, as noted above anchoring or sealing member 222 is engaged to the inside of a blood vessel or other tissue portion adjacent a hole to be closed. Stem 224, filament 226, and discs 270, 271 and buffer 260 along stem 224 and/or filament 226, extend proximally into or through an opening in the skin to the hole. Pusher 230 is moved forward along filament 226 and stem 224 (in the illustrated embodiment) to force locking disc 271, buffer material 260, holding disc 279 (if needed), and/or other parts forward. As pusher 230 moves forward, its pushing end 242 engages disc 271 to push it and the noted parts along filament 226 and/or stem 224. Indicator 250 remains fixed to filament 226 and/or stem 224, and so pusher 230 moves over indicator 250 as well, so that eventually proximal portion 252 of indicator 250 is exposed (or further exposed) from the proximal end 238 of pusher 230 as pusher 230 is moved forward. When the user sees contrasting part 256 emerge from pusher 230, whether part 256 is at the end of indicator 250 or a distance from the end, it is known that end 242 of pusher 230 has pushed locking disc 271, buffer 260 and any other items into a fully-deployed state, so that member 222 is locked in place and the hole is covered or sealed.

As pusher 230 is used as indicated, end 212 and tapering outer surface 210 lead within the opening in the skin. The taper of surface 210 allows pusher 230 to move through the skin opening with less likelihood of catching or snagging on tissue plane(s) adjoining the opening. Rather, tapering outer surface 210, to the extent necessary, provides a smooth adjustment of tissue plane(s) and/or dilation of the opening through them.

While description of particular embodiments (e.g. multiple connections for anchoring or sealing members) has been made above, it will be understood that other embodiments (such as single connections and other types of anchoring or sealing members) can be used. For example, features similar or related to those shown in this disclosure are also shown and described in commonly-owned application Ser. No. 13/111,338 (filed on May 19, 2011) and Ser. No. 13/303,707 (filed on Nov. 23, 2011), which are incorporated herein by reference in their entireties, and such features can be used with or in place of features disclosed herein.

While the disclosure has been illustrated and described in detail in the drawings and foregoing description, the same is to be considered as illustrative and not restrictive in character, it being understood that only the most preferred embodiments have been shown and described, and that all changes and modifications that come within the spirit of the disclosure are desired to be protected. For example, elongated members 24 may be placed in alternative configurations with respect to the rest of member 22, such as having two elongated members 24 adjacent ends 39 and on major axis MA, and two elongated members 24 offset from major axis MA so that a line between them is through center 38 and substantially perpendicular to axis MA. Further, features or aspects discussed in connection or in the context of one embodiment or part may be used with or incorporated into other embodiments, parts or aspects of this disclosure. In addition, all publications cited herein are indicative of the abilities of those of ordinary skill in the art and are hereby incorporated by reference in their entirety as if individually incorporated by reference and fully set forth.

What is claimed is:

1. A medical treatment device for closing a tissue opening in a patient, comprising:
    an anchoring member adapted to be positioned on one side of the tissue opening and to engage tissue bordering the tissue opening on the one side to close the tissue opening, the anchoring member including a wall, the wall having a valve portion allowing penetration through the wall and providing hemostatic control, the anchoring member including at least first and second stems separate from each other and wherein the first stem is offset laterally in a first direction from a center point of the anchoring member, and the second stem is offset laterally in a second direction from the center point, the first and second direction substantially opposed to each other; and
    first and second filaments connected to the anchoring member and adapted to extend from the anchoring member to a position outside of the patient so that pulling one or more of the filaments tends to engage or press the anchoring member against the tissue to seal the tissue opening; and
    wherein the device is sized and configured to close a hole formed in a wall of a blood vessel for a catheterization.

2. The device of claim 1, further comprising a pusher with a lumen, the pusher configured to move over at least part of the anchoring member.

3. The device of claim 2, wherein the pusher is configured to move over at least one of said stems and filaments, and further comprising an indicator fixed with respect to said at least one of said stems and filaments and at least partially within the pusher, the indicator having at least a portion contrasting with the pusher, wherein the indicator is positioned to exit from the pusher as the pusher is moved along said at least one of so that the contrasting portion exits from the pusher at a point at which the pusher has moved a desired distance.

4. The device of claim 2, wherein the pusher has a forward portion that is inwardly tapered.

5. The device of claim 1, wherein the first and second stems and the valve are along a line.

6. The device of claim 5, wherein a first distance between the first stem and the valve and a second distance between the second stem and the valve are substantially the same.

7. The device of claim 5, wherein the distance between the first and second stems is equal to or less than a dimension of the tissue opening.

8. The device of claim 5, wherein the first filament is connected to the first stem and the second filament is connected to the second stem.

9. The device of claim 1, at least one of said filaments is offset from the valve.

10. The device of claim 1, further comprising a guide wire inserted through the valve so that a portion of the guide wire is on opposite sides of the wall, wherein when the anchoring member is engaged with tissue bordering the tissue opening, a portion of the guide wire extends through the opening.

11. The device of claim 1, wherein:
    the first stem extends through a first hole in the wall, the first stem including a seal fixed to a distal end of said first stem and configured to cover the first hole, wherein the first stem is not fixed with respect to the anchoring member and can move through the first hole.

12. The device of claim 11, wherein the second stem extends through a second hole in the wall, the second stem including a seal fixed to a distal end of said second stem and configured to cover the second hole, wherein the second stem is not fixed with respect to the anchoring member and can move through the second hole.

13. The device of claim 1, wherein the anchoring member has a rim configured to engage tissue bordering the tissue opening on the one side.

14. A medical treatment device for closing a tissue opening in a patient, comprising:
- an anchoring member adapted to be positioned on one side of the tissue opening and to engage tissue bordering the tissue opening on the one side to close the tissue opening, the anchoring member including a wall, the anchoring member including at least first and second stems separate from each other and wherein the first stem is offset laterally in a first direction from a center point of the anchoring member, and the second stem is offset laterally in a second direction from the center point, the first and second direction substantially opposed to each other;
- first and second filaments connected to the anchoring member and adapted to extend from the anchoring member to a position outside of the patient so that pulling one or more of the filaments tends to engage or press the anchoring member against the tissue to seal the tissue opening; and
- a pusher with a lumen, the pusher configured to move over at least part of the anchoring member; and
wherein the device is sized and configured to close a hole formed in a wall of a blood vessel for a catheterization.

15. The device of claim 14, wherein the pusher is configured to move over at least one of said stems and filaments, and further comprising an indicator fixed with respect to said at least one of said stems and filaments and at least partially within the pusher, the indicator having at least a portion contrasting with the pusher, wherein the indicator is positioned to exit from the pusher as the pusher is moved along said at least one of said stems and filaments so that the contrasting portion exits from the pusher at a point at which the pusher has moved a desired distance.

16. The device of claim 14, wherein the distance between the first and second stems is equal to or less than a dimension of the tissue opening.

17. The device of claim 14, wherein the first filament is connected to the first stem and the second filament is connected to the second stem.

18. The device of claim 14, wherein the anchoring member has a rim configured to engage tissue bordering the tissue opening on the one side.

* * * * *